(12) United States Patent
Kushnir

(10) Patent No.: US 12,397,018 B2
(45) Date of Patent: *Aug. 26, 2025

(54) COAGULATION MOLD, A KIT AND A METHOD FOR PREPARING A COAGULATED BLOOD MASS

(71) Applicant: Reddress Ltd., Pardes Hana (IL)

(72) Inventor: Alon Kushnir, Givat Ada (IL)

(73) Assignee: Reddress Ltd., Pardes Hana (IL)

(*) Notice: Subject to any disclaimer, the term of this patent is extended or adjusted under 35 U.S.C. 154(b) by 0 days.

This patent is subject to a terminal disclaimer.

(21) Appl. No.: 18/783,156

(22) Filed: Jul. 24, 2024

(65) Prior Publication Data

US 2024/0374636 A1    Nov. 14, 2024

Related U.S. Application Data

(63) Continuation of application No. PCT/IL2023/050083, filed on Jan. 25, 2023.

(30) Foreign Application Priority Data

Jan. 25, 2022 (IL) .......................................... 290122

(51) Int. Cl.
| | |
|---|---|
| *A61K 35/14* | (2015.01) |
| *A61K 47/02* | (2006.01) |
| *A61K 47/14* | (2017.01) |

(52) U.S. Cl.
CPC .............. *A61K 35/14* (2013.01); *A61K 47/02* (2013.01); *A61K 47/14* (2013.01)

(58) Field of Classification Search
CPC ......... A61K 35/14; A61K 47/02; A61K 47/14
See application file for complete search history.

(56) References Cited

U.S. PATENT DOCUMENTS

| | | |
|---|---|---|
| 9,180,142 B2 | 11/2015 | Kushnir et al. |
| 10,111,979 B2 | 10/2018 | Kushnir et al. |
| 2015/0044272 A1* | 2/2015 | Kushnir .................. A61L 15/44 424/529 |
| 2020/0281775 A1 | 9/2020 | Kushnir et al. |

FOREIGN PATENT DOCUMENTS

| | | |
|---|---|---|
| WO | 2010/086848 A2 | 8/2010 |
| WO | 2019/150355 A1 | 8/2019 |

OTHER PUBLICATIONS

Kushnir et al., Wounds, 2016, vol. 28(9):317-327.*
Kushnir, I., et al., "Efficacy and Safety of a Novel Autologous Wound Matrix in the Management of Complicated, Chronic Wounds: A Pilot Study", Wounds: a Compendium of Clinical Research and Practice, Sep. 2016, 28 (9):317-327.
Thomas, S., et al., "The safety of an autologous whole blood clot product applied to full thickness dermal wounds in a porcine model for up to 18 days", Chronic Wound Care Management and Research, Jun. 19, 2019, 6:39-49.
International Search Report and Written Opinion of the ISA/EP in parent application PCT/IL2023/050083, Mar. 17, 2023, 10 pages.
PCT Chapter II Demand and Article 34 Claim Amendment filed in parent application PCT/IL2023/050083, Nov. 13, 2023, 19 pages.
Second Written Opinion of the IPEA/EP in parent application PCT/IL2023/050083, Apr. 10, 2024, 9 pages.
International Preliminary Report on Patentability of the IPEA/EP in parent application PCT/IL2023/050083, Apr. 30, 2024, 9 pages.
Mohamed et al., Sci. Rep., 2025, vol. 15, Article No. 2993.
Hazardous Substance Fact Sheet: Calcium Hydride (New Jersey Department of Health and Senior Services) (Mar. 2000).
Snyder et al., J. Wound Care, Sep. Sep. 2, 2024, vol. 33(9):688-700.

* cited by examiner

*Primary Examiner* — Xiaozhen Xie
(74) *Attorney, Agent, or Firm* — ICE MILLER LLP; Justin D. Swindells

(57) ABSTRACT

The present disclosure provides a method, a coagulation mold and a kit for preparing a coagulated blood mass having a desired shape and volume. The coagulated blood mass is prepared from whole blood being withdrawn from a subject. The whole blood is mixed with coagulation initiators in order to obtain the coagulated blood mass with optimal parameters. This is obtained, inter alia, by selecting particle size of one of the coagulation initiators such as to yield more rapid dissolving within the blood and/or to yield improved suspension of the particles in the blood when it is still in a liquid form. By controlling theses parameters, an optimal coagulated blood mass is obtained that can be used for treatment of the human body, e.g. for treating skin lesions, internal injuries, such as anal fistula, stoma cavity, damaged tendon, and others.

12 Claims, 1 Drawing Sheet

Time zero – Left<25micron right>25micron

Time 15min - Left<25micron right>25micron

COAGULATION MOLD, A KIT AND A METHOD FOR PREPARING A COAGULATED BLOOD MASS

CROSS-REFERENCE TO RELATED APPLICATIONS

This application is a continuation of International Application No. PCT/IL2023/050083 filed Jan. 25, 2023, which claims priority to Israel patent application number 290122 filed Jan. 25, 2022, the disclosures of which are incorporated herein by reference in their entirety.

TECHNOLOGICAL FIELD

The present disclosure is in the field of preparation of medical treatment, in particular preparation of a coagulated blood mass for use in a treatment of a subject.

BACKGROUND ART

References considered to be relevant as background to the presently disclosed subject matter are listed below:
U.S. Pat. No. 9,180,142
US 2020/0281775
WO 2019/150355

Acknowledgement of the above references herein is not to be inferred as meaning that these are in any way relevant to the patentability of the presently disclosed subject matter.

GENERAL DESCRIPTION

The present disclosure provides a method, a coagulation mold and a kit for preparing a coagulated blood mass, namely blood clot having a desired shape and volume. The coagulated blood mass is prepared from whole blood being withdrawn from a subject. The whole blood is mixed with coagulation initiators, i.e. coagulation agents or anti-anti coagulation agents, in a specific amount and having specific characteristics in order to obtain the coagulated blood mass with optimal parameters, such as stability, moisture, homogeneousness, namely the texture of the clot is substantially similar at any portion thereof, etc. This is obtained, inter alia, by selecting particle size of one of the coagulation initiators such as to yield more rapid dissolving within the blood and/or to yield improved suspension of the particles in the blood when it is still in a liquid form. Another parameter to yield the desired coagulated blood mass of the present invention is the selected amount of material of coagulation initiator to be mixed with the whole blood. By controlling theses parameters, an optimal coagulated blood mass is obtained that can be used for treatment of the human body, e.g. for treating skin lesions, internal injuries (such as anal fistula, stoma cavity, damaged tendon, etc.).

Thus, a first aspect of the present disclosure provides a method for preparing a coagulated blood mass, i.e. a volumetric blood clot, for use in a treatment of a lesion or injury of a subject. The treatment can be on the external portion of the body such as skin lesions or on internal portions of the body such as fistula cavity, abdominal cavity, etc. The method comprising: mixing an amount of whole blood with calcium gluconate powder and kaolin powder; and allowing the whole blood to coagulate to form the coagulated blood mass. The term "allowing" defines that the mixture of blood with maintaining the mixture of whole blood with calcium gluconate powder and kaolin powder is maintained for a selected amount of time until the blood solidifies to a certain degree and seize to be in a flowable form. The amount of time can be more than 1 minute, 2, 3, 4, 5, 6, 7, 8, 9, 10 or even more than 15 minutes until the whole blood is solidified to the desired degree. The method is further characterized by at least one of: (i) the particle-size distribution D50 of the calcium gluconate powder is between 50μ-200μ, (ii) wherein said mixing comprises mixing between 0.6 mg-3.1 mg of kaolin powder with every 1 ml of whole blood, (iii) wherein said mixing comprises mixing between 2.5 mg-8.1 mg of calcium gluconate powder with every 1 ml of whole blood, or (iv) the particle-size distribution D50 of the kaolin powder is less than 20μ.

The particle-size distribution DX means that X % of the particles in the powder are less than the nominal size associated with said distribution. For example, if the particle-size distribution D50 is 125μ then 50% of the particles are having a volumetric size equal or less to 125μ. By maintaining only particles with size that is relatively small, the resulted coagulated blood mass is homogenous, namely the volumetric solidity of the coagulated blood mass is substantially equal. This is resulted due to the duration that particles with such a size can suspend in the whole blood they are mixed with. Larger particles tend to sink in the blood and the resulted coagulated blood mass is not homogeneous.

It is to be noted that any combination of the described embodiments with respect to any aspect of this present disclosure is applicable. In other words, any aspect of the present disclosure can be defined by any combination of the described embodiments.

In some embodiments of the method, the particle-size distribution D70 of the calcium gluconate powder is between 50μ-200μ.

In order to prepare a coagulated blood mass with properties that are suitable for using in a medical treatment the calcium gluconate powder is first milled to a size of 2μ. The particles product of this milling is typically undergoing a certain degree of granulation, thus prior to the use of the powder in the formation of the coagulated blood mass, the calcium gluconate powder is sifted through a sifter of 120-125μ particles. Particle size of less than 120-125μ dissolve much faster and therefore the use thereof in the formation of a coagulated blood mass results in a much more stable and non-leaky coagulated blood mass.

In some embodiments of the method, particle-size distribution D90 of the calcium gluconate powder is between 50μ-200μ.

In some embodiments of the method, the particle-size distribution D90, D80, D70, D60, or D50 of the calcium gluconate powder is about 125μ.

The term "about" should be understood as a deviation of up to 20% from the nominal value. For example, if the nominal value is about 125μ, then the value should be considered as 100μ-150μ.

In some embodiments of the method, the particle-size distribution of either D50, D60, D70, D80, D90 or D95 of the calcium gluconate powder is between either 50μ-200μ, 60μ-190μ, 70μ-180μ, 80μ-170μ, 90μ-160μ, 100μ-150μ, 110μ-140μ or 120μ-130μ.

In some embodiments of the method, the particle-size distribution D99 of the kaolin powder is less than 50μ.

In some embodiments of the method, the particle-size distribution D99 of the kaolin powder is less than 50μ.

By using small particles of kaolin in the preparation of the coagulated blood mass, the kaolin particles suspend for a longer duration in the formed coagulating blood mass (when at least some of the blood is in liquid flowable form) and do not sink rapidly to the bottom of the formed coagulating blood mass, therefore resulting in a substantive homogeneous coagulated blood mass.

In some embodiments of the method, the particle-size distribution D80 of the kaolin powder is less than 25μ.

In some embodiments of the method, the particle-size distribution D90 of the kaolin powder is less than 3μ or between 1μ-3μ.

In some embodiments of the method, the particle-size distribution of either D50, D60, D70, D80, D90 or D95 of the calcium gluconate powder is less than either 30μ, 25μ, 20μ, 15μ, 10μ, 5μ, 3μ, 2μ, 1μ or less than 0.1μ.

In some embodiments, the method comprising withdrawing said whole blood from the subject, therefore the coagulated blood mass is prepared from autologous whole blood.

In some embodiments, the method comprising, prior to said mixing, introducing anti-coagulant-containing liquid to said amount of whole blood. Namely, after the whole blood is withdrawn, it is added with anti-coagulant to prevent undesired coagulation of the blood.

In some embodiments of the method, said introducing comprises introducing between 0.04 ml-0.095 ml of anti-coagulant-containing liquid for every 1 ml of whole blood.

In some embodiments of the method, said introducing comprises introducing about 0.07 ml of anti-coagulant-containing liquid for every 1 ml of whole blood.

In some embodiments of the method, said mixing is performed within a coagulation mold. The coagulation mold has a desired shape that determines the shape of the blood clot being prepared by the method.

In some embodiments of the method, the mixing comprises mixing between 0.6 mg-3.1 mg of kaolin powder with every 1 ml of whole blood.

In some embodiments of the method, said mixing comprises mixing about 1.75 mg of kaolin powder with every 1 ml of whole blood.

In some embodiments of the method, said mixing comprises mixing between 0.8 mg-2.9 mg, 1 mg-2.7 mg, 1.2 mg-2.5 mg, 1.4 mg-2.3 mg, 1.6 mg-2.1 mg or 1.8 mg-2 mg of kaolin powder with every 1 ml of whole blood.

In some embodiments of the method, said mixing comprises mixing between 2.5 mg-8.1 mg of calcium gluconate powder with every 1 ml of whole blood.

In some embodiments of the method, said mixing comprises mixing about 5.3 mg of calcium gluconate powder with every 1 ml of whole blood.

In some embodiments of the method, said mixing comprises mixing between 2.9 mg-7.7 mg, 3.3 mg-7.3 mg, 3.7 mg-6.9 mg, 4.1 mg-6.5 mg, 4.5 mg-6.1 mg or 4.9 mg-5.7 mg of calcium gluconate powder with every 1 ml of whole blood.

Yet another aspect of the present disclosure provides a coagulation mold comprising a coagulation space defined by a base surrounded by upwardly rising walls and configured to receive a selected amount of whole blood. The coagulation space comprises calcium gluconate powder and kaolin powder. The coagulation mold comprises at least one of the following: (i) the particle-size distribution D50 of the calcium gluconate powder between 50μ-200μ, (ii) kaolin powder in an amount of between 0.6 mg-3.1 mg for every 1 ml of said selected amount of whole blood, (iii) calcium gluconate in an amount of between 2.5 mg-8.1 mg for every 1 ml of said selected amount of whole blood, or (iv) the particle-size distribution D50 of the kaolin powder is less than 10μ.

In some embodiments of the coagulation mold, the particle-size distribution D70 of the calcium gluconate powder is between 50μ-200μ.

In some embodiments of the coagulation mold, the particle-size distribution D90 of the calcium gluconate powder is between 500μ-200μ.

In some embodiments of the coagulation mold, the particle-size distribution D90, D80, D70, D60, or D50 of the calcium gluconate powder is about 125μ.

In some embodiments of the coagulation mold, the particle-size distribution of either D50, D60, D70, D80, D90 or D95 of the calcium gluconate powder is between either 50μ-200μ, 60μ-190μ, 70μ-180μ, 80μ-170μ, 90μ-160μ, 100μ-150μ, 110μ-140μ or 120μ-130μ.

In some embodiments of the coagulation mold, the particle-size distribution D99 of the kaolin powder is less than 50μ.

In some embodiments of the coagulation mold, the particle-size distribution D90 of the kaolin powder is less than 20μ or less than 10μ.

In some embodiments of the coagulation mold, the particle-size distribution D50 of the kaolin powder is less than 3μ or between 1μ-3μ.

In some embodiments of the coagulation mold, the particle-size distribution of either D50, D60, D70, D80, D90 or D95 of the calcium gluconate powder is less than either 30μ, 25μ, 20μ, 15μ, 10μ, 5μ, 3μ, 2μ, 1μ or less than 0.1μ.

In some embodiments of the coagulation mold, the whole blood being intended to be received therein comprises between 0.04 ml-0.095 ml of anti-coagulant-containing liquid for every 1 ml of whole blood or in some embodiments about 0.07 ml of anti-coagulant-containing liquid for every 1 ml of whole blood.

In some embodiments, the coagulation mold comprising between 0.6 mg-3.1 mg of kaolin powder for every 1 ml of said selected amount of whole blood.

In some embodiments, the coagulation mold comprising about 1.75 mg of kaolin powder for every 1 ml of said selected amount of whole blood.

In some embodiments, the coagulation mold comprising between 0.8 mg-2.9 mg, 1 mg-2.7 mg, 1.2 mg-2.5 mg, 1.4 mg-2.3 mg, 1.6 mg-2.1 mg or 1.8 mg-2 mg of kaolin powder with every 1 ml of whole blood.

In some embodiments, the mold comprising between 2.5 mg-8.1 mg of calcium gluconate powder for every 1 ml of said selected amount of whole blood.

In some embodiments, the mold comprising about 5.3 mg of calcium gluconate powder for every 1 ml of said selected amount of whole blood.

In some embodiments, the coagulation mold comprising 2.9 mg-7.7 mg, 3.3 mg-7.3 mg, 3.7 mg-6.9 mg, 4.1 mg-6.5 mg, 4.5 mg-6.1 mg or 4.9 mg-5.7 mg of calcium gluconate powder with every 1 ml of whole blood.

In some embodiments of coagulation mold, the volume of the coagulation space is sufficient to receive between 13 ml-19 ml of whole blood.

In some embodiments of coagulation mold, the volume of the coagulation space is sufficient to receive about 16 ml of whole blood.

Yet another aspect of the present disclosure provides a kit for preparing a coagulated blood mass comprising: calcium gluconate powder; kaolin powder; and a coagulation mold for mixing a selected amount of blood with the calcium gluconate powder and kaolin powder. The calcium gluconate powder and the kaolin powder are characterized by at least one of the following: (i) the particle-size distribution D50 of the calcium gluconate powder is between 50μ-200μ, (ii) wherein said kaolin powder is an amount of between 0.6 mg-3.1 mg for every 1 ml of said selected amount of whole blood, (iii) wherein said calcium gluconate is an amount of between 2.5 mg-8.1 mg for every 1 ml of said selected amount of whole blood, or (iv) the particle-size distribution D50 of the kaolin powder is less than 10μ.

In some embodiments, the kit comprising tools for withdrawing whole blood and containing it.

In some embodiments, the kit comprising 0.04 ml-0.095 ml of anti-coagulant-containing liquid for every 1 ml of said selected amount of whole blood. The anti-coagulant-containing liquid can be contained separately in the kit or within the tool for containing the withdrawn whole blood.

In some embodiments of the kit, said selected amount is between 13 ml-19 ml.

In some embodiments of the kit, the particle-size distribution D70 of the calcium gluconate powder is between 50μ-200μ.

In some embodiments of the kit, the particle-size distribution D90 of the calcium gluconate powder is between 50μ-200μ.

In some embodiments of the kit, the particle-size distribution D90, D80, D70, D60, or D50 of the calcium gluconate powder is about 125μ.

In some embodiments of the kit, the particle-size distribution of either D50, D60, D70, D80, D90 or D95 of the calcium gluconate powder is between either 50μ-200μ, 60μ-190μ, 70μ-180μ, 80μ-170μ, 90μ-160μ, 100μ-150μ, 110μ-140μ or 120μ-130μ.

In some embodiments of the kit, the particle-size distribution D99 of the kaolin powder is less than 50μ.

In some embodiments of the kit, the particle-size distribution D80 of the kaolin powder is less than 10μ.

In some embodiments of the kit, the particle-size distribution D50 of the kaolin powder is less than 3μ or between 1μ-3μ.

In some embodiments of the kit, the particle-size distribution of either D50, D60, D70, D80, D90 or D95 of the calcium gluconate powder is less than either 30μ, 25μ, 20μ, 15μ, 10μ, 5μ, 3μ, 2μ, 1μ or less than 0.1μ.

In some embodiments, the kit comprising between 0.6 mg-3.1 mg of kaolin powder for every 1 ml of said selected amount of whole blood.

In some embodiments, the kit comprising about 1.75 mg of kaolin powder for every 1 ml of said selected amount of whole blood.

In some embodiments, the kit comprising between 0.8 mg-2.9 mg, 1 mg-2.7 mg, 1.2 mg-2.5 mg, 1.4 mg-2.3 mg, 1.6 mg-2.1 mg or 1.8 mg-2 mg of kaolin powder with every 1 ml of whole blood.

In some embodiments, the kit comprising between 2.5 mg-8.1 mg of calcium gluconate powder for every 1 ml of said selected amount of whole blood.

In some embodiments, the kit comprising about 5.3 mg of calcium gluconate powder for every 1 ml of said selected amount of whole blood.

In some embodiments, the kit comprising 2.9 mg-7.7 mg, 3.3 mg-7.3 mg, 3.7 mg-6.9 mg, 4.1 mg-6.5 mg, 4.5 mg-6.1 mg or 4.9 mg-5.7 mg of calcium gluconate powder with every 1 ml of whole blood.

In some embodiments, the kit comprising the coagulation mold of any one of the above-described embodiments or any combination thereof. The kaolin powder and calcium gluconate powder are comprised within said coagulation mold.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 1A shows the result in time zero and FIG. 1B shows the result in time 15 minutes.

DETAILED DESCRIPTION

Figure 1A:
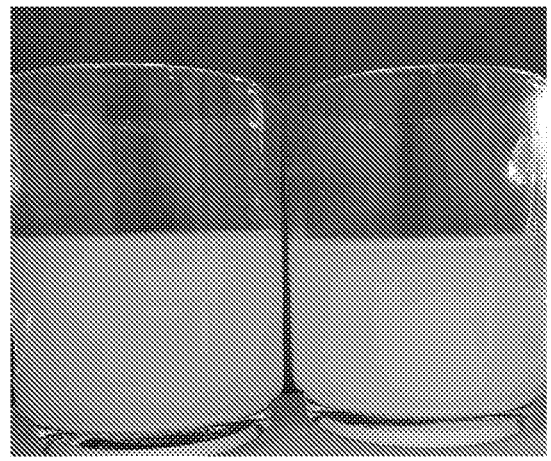
FIGS. 1A-1B are images of the results of the kaolin powder particle size test.

The following are examples of tests with varying parameters of the powders used in the method for forming a coagulated blood mass. These tests are provided to exemplify embodiments and realization of the invention of the present disclosure.

Calcium Gluconate (CG) Powder Test

Success Criteria:

Optimal Clot is Defined by:
  Coagulation time—good coagulation time is under 6 minutes
  Visual clot structure strength—good structure strength is defined as the clot does not break down when extracted and handled by user
  CG residuals—visual assessment of amount of white powder residuals accumulated on the bottom of the clot—0=no residuals, 5=100% coverage of surface with residuals Method:

A standard amount of ACD-A anticoagulant and Kaoiln powder per 1 ml of whole blood was used
  2 ml of ACD-A for 15 ml blood=0.133 ml ACD-A/1 ml blood
  28 mg Kaolin powder for 15 ml blood=1.87 mg Kaolin/1 ml blood Different amounts of CG where tested-CG particle size after sifting is 125 micron
  20 mg for 15 ml of blood=1.33 mgCG/1 ml blood
  50 mg for 15 ml of blood=3.33 mgCG/1 ml blood
  85 mg for 15 ml of blood=5.66 mgCG/1 ml blood
  110 mg for 15 ml of blood=7.33 mgCG/1 ml blood
  140 mg for 15 ml of blood=9.33 mgCG/1 ml blood Coagulation time and clot structure strength were documented. Blood samples of 5 different volunteers were used.

Results:

The following table describes the results of the test:

TABLE 1

| # volunteer/CG | Coagulation time | Clot strength | Powder residuals |
| --- | --- | --- | --- |
| #1/20 mg | 15 | Low | 0 |
| #1/50 mg | 6.8 | Medium | 0 |
| #1/85 mg | 4.7 | Strong | 0 |
| #1/110 mg | 5 | Strong | 2 |
| #1/140 mg | 4.9 | Strong | 5 |
| #2/20 mg | 17 | Low | 0 |
| #2/50 mg | 6.7 | Medium | 0 |
| #2/85 mg | 4.8 | Strong | 0 |
| #2/110 mg | 4.7 | Strong | 2 |
| #2/140 mg | 4.8 | Strong | 5 |
| #3/20 mg | 14 | Low | 0 |
| #3/50 mg | 5.4 | Medium | 0 |
| #3/85 mg | 4.6 | Strong | 1 |
| #3/110 mg | 5.2 | Strong | 2 |
| #3/140 mg | 4.7 | Strong | 5 |
| #4/20 mg | 12 | Low | 0 |
| #4/50 mg | 6 | Medium | 0 |
| #4/85 mg | 4.8 | Strong | 0 |
| #4/110 mg | 4.6 | Strong | 2 |
| #4/140 mg | 5 | Strong | 5 |
| #5/20 mg | 14.5 | Low | 0 |

TABLE 1-continued

| # volunteer/CG | Coagulation time | Clot strength | Powder residuals |
|---|---|---|---|
| #5/50 mg | 6.6 | Medium | 0 |
| #5/85 mg | 4.6 | Strong | 0 |
| #5/110 mg | 4.9 | Strong | 2 |
| #5/140 mg | 5.2 | Strong | 5 |
| Average/20 mg | 14.5 | Low | 0 |
| Average/50 mg | 6.3 | Medium | 0 |
| Average/85 mg | 4.88 | Strong | 0.2 |
| Average/110 mg | 4.7 | Strong | 2 |
| Average/140 mg | 4.92 | Strong | 5 |

Kaolin Powder Test
Success Criteria:
Optimal Clot is Defined by:
1. Coagulation time-good coagulation time is under 6 minutes
2. Visual clot structure strength-good structure strength is defined as the clot does not break down when extracted and handled by user Method:
A standard amount of ACD-A anticoagulant and Calcium Gluconate powder per 1 ml of whole blood was used
  2 ml of ACD-A for 15 ml blood=0.133 ml ACD-A/1 ml blood
  85 mg CG powder for 15 ml blood=5.66 mg CG/1 ml blood Different amounts of Kaolin where tested-Kaolin particle size is 1-3 micron
  5 mg for 15 ml of blood=1.33 mgCG/1 ml blood
  10 mg for 15 ml of blood=3.33 mgCG/1 ml blood
  20 mg for 15 ml of blood=5.66 mgCG/1 ml blood
  30 mg for 15 ml of blood=7.33 mgCG/1 ml blood
  40 mg for 15 ml of blood=9.33 mgCG/1 ml blood Coagulation time and clot structure strength were documented. Blood samples of 5 different volunteers were used.
Results:
The following table describes the results of the test:

TABLE 2

| # volunteer/Kaolin | Coagulation time | Clot strength |
|---|---|---|
| #1/5 mg | 12 | Low |
| #1/10 mg | 8.2 | Medium |
| #1/20 mg | 6.2 | Strong |
| #1/30 mg | 4.7 | Strong |
| #1/40 mg | 4.9 | Strong |
| #2/5 mg | 14 | Low |
| #2/10 mg | 8.5 | Medium |
| #2/20 mg | 5.8 | Strong |
| #2/30 mg | 5.1 | Strong |
| #2/40 mg | 5.5 | Strong |
| #3/5 mg | 11.5 | Low |
| #3/10 mg | 7.7 | Medium |
| #3/20 mg | 5.4 | Strong |
| #3/30 mg | 5.2 | Strong |
| #3/40 mg | 4.8 | Strong |
| #4/5 mg | 13.4 | Low |
| #4/10 mg | 8.5 | Medium |
| #4/20 mg | 6.3 | Strong |
| #4/30 mg | 4.9 | Strong |
| #4/40 mg | 5.2 | Strong |
| #5/5 mg | 14 | Low |
| #5/10 mg | 7.3 | Medium |
| #5/20 mg | 5.4 | Strong |
| #5/30 mg | 5.1 | Strong |
| #5/40 mg | 5.1 | Strong |
| Average/5 mg | 12.98 | Low |
| Average/10 mg | 8.04 | Medium |
| Average/20 mg | 5.82 | Strong |
| Average/30 mg | 5 | Strong |
| Average/40 mg | 5.1 | Strong |

Kaolin Powder Particle Size Test
Goal
The goal of the test is to establish effective threshold of Kaolin powder to float in water for sufficient time to allow coagulation of blood simultaneously in all volume at the same time.
Background
Blood coagulates rapidly via the extrinsic pathway when Kaolin or other coagulation initiator (such as glass) comes in contact with factor XI. The more Kaolin particles that come in contact with blood for more time, the higher probability of contact. Kaolin is a clay mineral that typically sink in water due to its weight. If Kaolin particles will be able to freely float in liquid it will have higher effect of coagulation, achieving an evenly distributed coagulation that starts at once in all the blood volume, similar in the upper part of the blood volume as in the lower part of the blood volume etc. The idea is that if kaolin particles are sufficiently small, they can float in the blood for a sufficient duration before they start to sink to allow homogenic coagulation initiation and acceleration, achieving a homogenic clot.
Success Criteria
  Kaolin particles float in liquid for 15 minutes without sinking
Method
  2 sizes of particles were tested
  Smaller than 25 micron
  Larger than 25 micron
For each group of particles size, 50 mg of powder was placed inside a clear glass vessel with 160 ml of purified water. Both glass vessels were mixed for 5 seconds with a steering spoon. At time points 0 and 15 minutes the vessels were visually assessed for the following parameters
1. Water color and transparency (from 10: white/non transparent to 1: Clear/Fully Transparent)
2. Accumulation of kaolin powder on the bottom of the vessel (From 10: No accumulation to 1: fully accumulated)

Figure 1B:
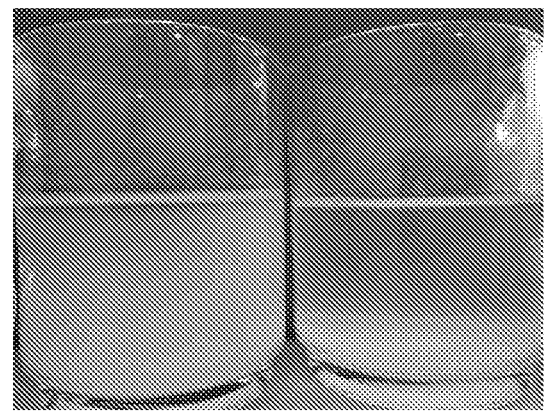

Results
The following table describes the results of the test (and also can be seen in FIGS. 1A-1B):

TABLE 3

| # | Water color&transparency | Accumulation on the bottom |
|---|---|---|
| Time0 Cup <25 micron | 10 | 10 |
| Time0 Cup >25 micron | 10 | 10 |
| Time15 min Cup <25 micron | 10 | 2 |
| Time15 min Cup <25 micron | 10 | 4 |

CONCLUSIONS

Kaolin particle size lower that 25 micron float in water and thus in blood for 15 minutes without sinking while kaolin particle larger than 25 micron will sink within timeframe of 15 minutes.

The invention claimed is:

1. A coagulation mold comprising:
a coagulation space defined by a base surrounded by upwardly rising walls and configured to receive a selected amount of whole blood; and
calcium gluconate powder and kaolin powder comprised within said coagulation space;
the coagulation mold being characterized in that:
(i) said calcium gluconate powder is in an amount of about 3.3 mg-7.3 mg per 1 ml of said selected amount of whole blood;
(ii) the particle-size distribution D50 of the calcium gluconate powder is about 50μ-200μ;
(ii) said kaolin powder is in an amount of about 0.6 mg-3.1 mg per 1 ml of said selected amount of whole blood; and
(iv) the particle-size distribution D50 of the kaolin powder is less than about 25μ.

2. The coagulation mold of claim 1, wherein the particle-size distribution of the calcium gluconate powder meets one of the criteria selected from (i) D70 of between about 50μ-200μ, (ii) D90 of between about 50μ-200μ, and (iii) D50 of about 125μ.

3. The coagulation mold of claim 1, wherein the particle-size distribution of the kaolin powder meets one of the criteria selected from (i) D99 of less than about 50μ, (ii) D80 of less than about 25μ, and (iii) D45 of less than about 3μ.

4. The coagulation mold of claim 1, comprising at least one of (i) about 1.75 mg of kaolin powder per 1 ml of whole blood, and (ii) about 5.3 mg of calcium gluconate powder per 1 ml of whole blood.

5. The coagulation mold of claim 1, wherein the volume of the coagulation space is sufficient to receive an amount of 13 ml-19 ml of whole blood.

6. A kit for preparing a coagulated blood mass comprising:
calcium gluconate powder;
kaolin powder; and
a coagulation mold for mixing a selected amount of whole blood with the calcium gluconate powder and kaolin powder;
the kit being characterized in that:
(i) said calcium gluconate powder is in an amount of about 3.3 mg-7.3 mg per 1 ml of said selected amount of whole blood;
(ii) the particle-size distribution D50 of the calcium gluconate powder is about 50μ-200μ;
(iii) said kaolin powder is in an amount of about 0.6 mg-3.1 mg per 1 ml of said selected amount of whole blood; and
(iv) the particle-size distribution D50 of the kaolin powder is less than about 25μ.

7. The kit of claim 6, further comprising tools for withdrawing whole blood and containing it.

8. The kit of claim 6, comprising about 0.04 ml-0.095 ml of anti-coagulant-containing liquid for every 1 ml of said selected amount of whole blood.

9. The kit of claim 6, wherein the particle-size distribution of the calcium gluconate powder meets one of the criteria selected from (i) D70 is between 50μ-200μ, (ii) D90 is between 50μ-200μ, and (iii) D50 is about 125μ.

10. The kit of claim 6, wherein the particle-size distribution of the kaolin powder meets one of the criteria selected from (i) D99 is less than about 50μ, (ii) D80 is less than about 25μ, and (iii) D45 is less than about 3μ.

11. The kit of claim 6, comprising at least one of (i) about 1.75 mg of kaolin powder per 1 ml of whole blood, and (ii) about 5.3 mg of calcium gluconate powder per 1 ml of whole blood.

12. The kit of claim 6, wherein said kaolin powder and calcium gluconate powder are comprised within said coagulation mold.

* * * * *